United States Patent [19]
Kurtze

[11] Patent Number: 5,176,676
[45] Date of Patent: Jan. 5, 1993

[54] PLUG CONNECTOR FOR A SURFACE ELECTRODE

[75] Inventor: Andreas Kurtze, Fritzens, Austria

[73] Assignee: D. Swarovski & Co., Wattens, Austria

[21] Appl. No.: 684,812

[22] Filed: Apr. 15, 1991

[30] Foreign Application Priority Data

Apr. 20, 1990 [AT] Austria ................. A922/90

[51] Int. Cl.⁵ .............................. A61B 17/39
[52] U.S. Cl. ..................... 606/32; 128/798; 439/492
[58] Field of Search ............... 606/32; 128/639, 640, 128/798, 802, 803; 439/492, 495, 496, 909

[56] References Cited

U.S. PATENT DOCUMENTS

| | | | |
|---|---|---|---|
| 3,159,447 | 12/1964 | Crimmins et al. | 439/496 X |
| 3,642,008 | 2/1972 | Bolduc | 606/32 X |
| 3,897,130 | 7/1975 | Donnelly et al. | 439/496 |
| 4,745,918 | 5/1988 | Feucht | 606/32 X |
| 4,873,973 | 10/1989 | Hagen | 606/32 |

FOREIGN PATENT DOCUMENTS 1441622  7/1976  United Kingdom ................. 128/639

Primary Examiner—Lee S. Cohen
Attorney, Agent, or Firm—Wenderoth, Lind & Ponack

[57] ABSTRACT

A flexible surface electrode for use in carrying current to and from the skin of a human body includes an insulating carrier having a projecting tongue and at least one electrically conductive foil on one side of the carrier and extending along the tongue. The tongue is bent around an end edge of a plate-shaped stiffening member with the foil facing outwardly and away from the end edge of the stiffening member. A clamping plate clamps an end portion of the tongue against the stiffening member, with the foil still being exposed at the end edge thereof. A cover plate covers that portion of the tongue extending from the end edge of the stiffening member toward the remainder of the carrier and the electrode.

19 Claims, 5 Drawing Sheets

PLUG CONNECTOR FOR A SURFACE ELECTRODE

BACKGROUND OF THE INVENTION

The invention relates to a flexible surface electrode for carrying current to and from the skin of a human body and in the form of an insulated carrier which is covered with at least one electrically conductive foil which extends into a tongue projecting from the surface electrode, wherein the tongue is bent around a stiffening plate-like shaped portion in such a way that the electrically conductive foils face outwardly. The invention further relates to a plug connector for use with such a surface electrode.

With regard to surface electrodes as are used in particular as neutral electrodes in surgery, there is a wish for a connection, which can be made quickly but which is nonetheless secure, to the plug connector which is associated with the electrode. It has been found to be disadvantageous for the contact tongue of the surface electrode to be just as flexible as the electrode itself as it bends easily upon being inserted into a contact sleeve or upon being connected to a connecting clamp of the connector (DE-A-37 39 516).

DE-A-35 44 483 discloses a flexible surface electrode in which the conductive surface of the tongue is bent around an end edge of a shaped portion and thereby stiffened. However, contact with the tongue does not occur in the region of the end edge but in the end region of the tongue which extends parallel to the sleeve. In such arrangement, the conductive portion of the tongue is brought into force-locking contact by means of a spring-loaded pressure member with conductive layers provided on the wall of the sleeve. The spring-loaded pressure member quite considerably increases the structural height of the plug connector. In addition, the plug connector disclosed in DE-A-35 44 483 suffers from the disadvantage that the limit position of the tongue in the sleeve is not defined with sufficient degree of accuracy. Electrical contact still is made when the tongue is partially pulled out. That means that the conductive part of the surface of the tongue can come into contact directly with the skin of the patient. However, only a part of the electrode, the electrical resistance of which is substantially higher than that of the contact surfaces of the tongue is suitable for making contact with the skin.

SUMMARY OF THE INVENTION

The invention avoid such problem in that the end of the tongue is retained between the shaped portion and a clamping plate, that the electrically conductive foils are exposed for contact purposes at the end edge of the shaped portion, and that the part of the tongue which extends between the end edge of the shaped portion and the remainder of surface electrode is covered by a cover plate.

The fact that, in accordance with the invention, the parts of the contact tongue which are remote from the end edge of the shaped portion are covered, means that there is no danger if the contact tongue is pulled out slightly of the corresponding plug connector. With the construction according to the invention, electrical contact is interrupted when the tongue is pulled out even slightly, for which reason it is particularly advantageous if provided on the shaped portion, the clamping plate or the cover plate, are openings or projections for positive connection to corresponding projection or openings on the plug connector.

WO 81/01646 discloses a plug connector of such type, but that suffers from the disadvantage that the plug connector is of relatively large structural height. That is to be attributed to the fact that the electrically conductive portion of the tongue extends entirely at the top side of the stiffening shaped portion so that the resilient contact terminal must be arranged between the top side of the tongue and the inside wall of the sleeve.

The invention therefore permits the plug connector to be of a flat configuration, thereby avoiding painful pressure points which occur when the patient lies on conventional devices.

Contact with the tongue in accordance with the invention can be effected, for example, by a spring clip which opens outwardly in a mouth-like configuration and which is provided in the interior of the sleeve or socket of the plug connector. Particularly when the edge of the shaped portion of the tongue converges in the manner of a cutting edge, a spring clip of such type readily can be provided with a space in cross section which precisely corresponds to that of the stiffened tongue. The sleeve or socket of the plug connector can therefore be of an internal width which precisely corresponds to the external contour of the stiffened tongue. Such arrangement prevents the penetration of liquid into the plug connector and resulting leakage of currents to the exterior.

The positive connection between the shaped portion on the one hand and the sleeve or socket of the plug connector on the other hand can be made in quite different ways. However, to provide the desired low structural dimension of the sleeve, it is particularly advantageous if the shaped portion is positively anchored at the outer side edges of the sleeve. That can be achieved by, for example, providing the above mentioned projections to prevent the shaped portions from being pulled on arms which are connected to the shaped portion by limbs and which extend parallel to longitudinal direction of the tongue.

Various structural configurations can be envisaged with regard to the design of the shaped portion for stiffening the tongue. If there is a wish to prevent the free end of the tongue from sticking, it is advantageous for the shaped portion to be connected by way of a film or flexible hinge to a clamping plate which presses against the end of the tongue. Covering of the conductive portion of the tongue in the region between the remainder of the electrode and the exposed contact surface is also advantageously effected by way of a cover plate pivotably connected to the shaped portion.

BRIEF DESCRIPTION OF THE DRAWINGS

Other objects, features and advantages of the invention will be apparent from the following description, taken with the accompanying drawings, wherein.

DETAILED DESCRIPTION OF THE INVENTION

Figure 1:
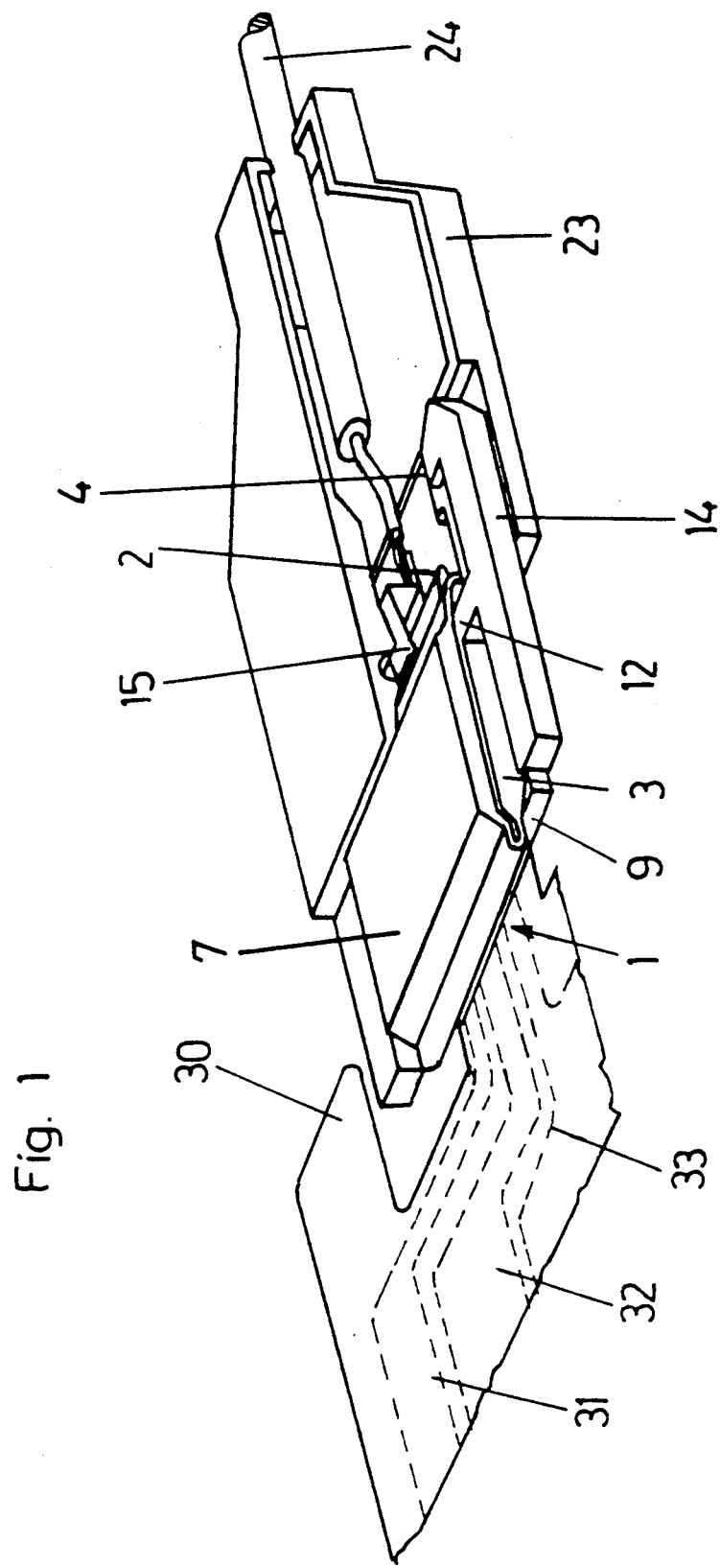
FIG. 1 is a perspective view showing that part of a surface electrode which is essential to the invention in connection with a plug connector which is shown partly in section.

A plug connector 23 shown in FIG. 1 serves to make contact by way of a cable 24 and a spring clip 15 with a surface electrode of which only part is shown. The electrode essentially comprises a carrier 30 which is to be stuck to the skin of the patient and to the underside of which are applied conductive foils 31-33 which extend into a tongue 1. The surface electrode is provided with at least one tongue 1 which conducts at the underside thereof. A stiffening member or shaped portion 3 serves to stiffen the tongue 1, the tongue 1 being bent around an end edge 2 of the shaped portion 3. Contact between the connector 2 and the tongue 1 occurs in the region of the edge 2.

In order for the tongue 1 to be positively secured in the plug connector 23, openings 13 are provided at the outside of a sleeve or socket 5 of the plug connector 23. Engaging into the opening 13 are corresponding projections 4 which can be removed from the openings 13 by compressing the arms 14. When that occurs, limbs 12 which connect the arms 14 to the shaped portion 3 experience resilient deformation. When the shaped portion 3 is pushed into an opening 25 of the sleeve 5, the limbs 12 form an abutment which abut with the end of the sleeve, thus precisely establishing the limit position of the tongue 1. In that limit position the spring clip 15, which opens outwardly in a mouth-like configuration, bears resiliently against the tongue 1 in the region of the end edge 2 of the shaped portion 3.

Figure 2:
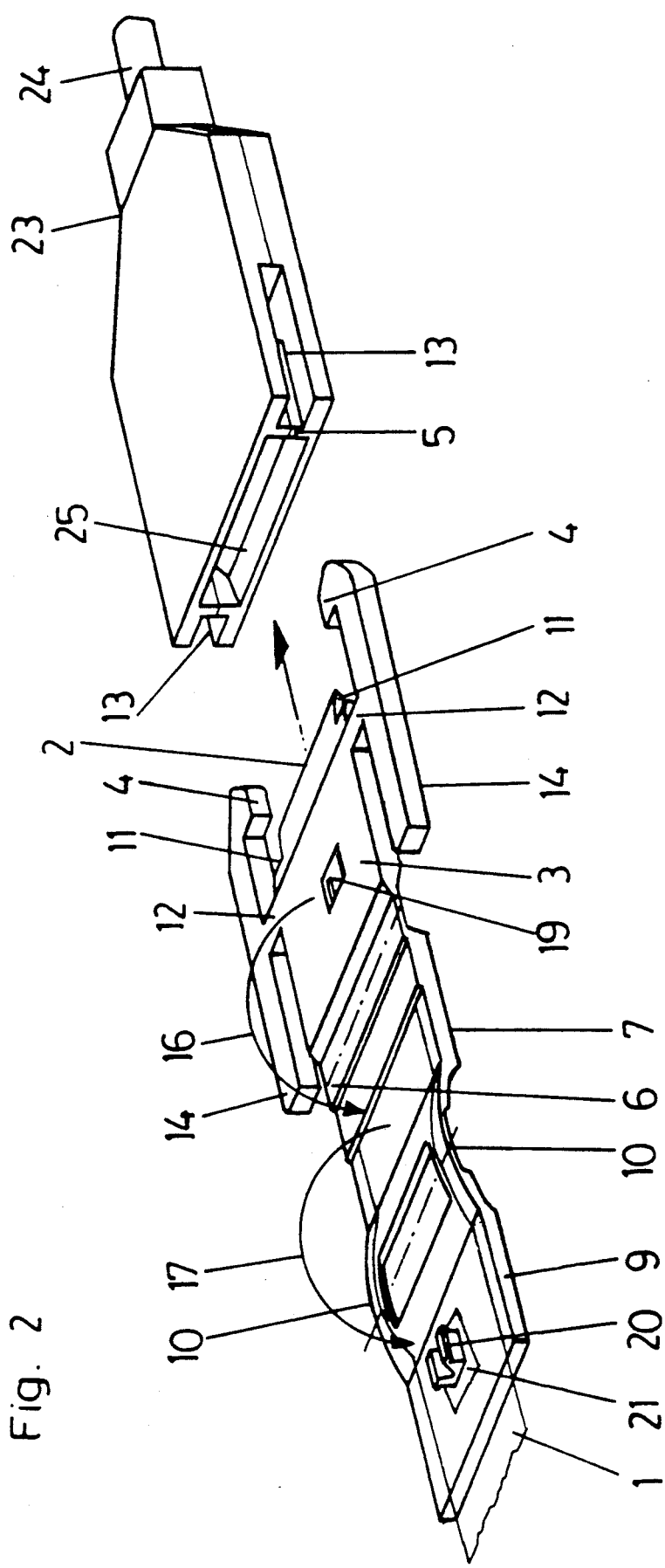
FIG. 2 is a similar view showing the parts illustrated in FIG. 1 separately prior to fixing of a tongue to a shaped portion.

FIG. 2 shows the way in which the tongue 1 is connected to the shaped portion 3 shown in FIG. 1. Firstly the tongue 1, with the conductive side downwardly, is laid on to those parts which are finally intended to function as a clamping plate 7 and a cover plate 9, When that is done, a press fastener 20 passes through an opening 21 in the tongue 1 which has its conductive side facing downwardly. The shaped portion 3 is now firstly pivoted about a flexible film hinge 6 connecting portion 3 with plate 7 in the direction indicated by the arrow 16, whereby a free edge of the tongue 1 is pressed against the shaped portion 3 by the clamping plate 7. Further pivotal movement of the two portions 3 and 7, which bear against each other, about the longitudinal center of curved portions 10, results in the situation shown in FIG. 1, in which the shaped portion 3 is positioned over and connected to the cover plate 9 which protects the conductive underside of the tongue 1, as the press fastener 20 is engaged into a retaining opening 19 in the shaped portion 3. The curved portions 10 are disposed in recesses 11 in opposite sides of the end edge 2 of the shaped portion 3, and edge 2 fits through an opening between portions 10. The conductive underside of the tongue 1 surrounds the end edge 2 of the shaped portion 3, and end edge 2 converges in a cutting edge-like configuration, so that contact can there be made with the spring clip or slips 15 of the plug connector 23. If the foils 31-33 are not connected together, then it will be appreciated that a spring clip 15 must be provided for each foil.

Figure 3:
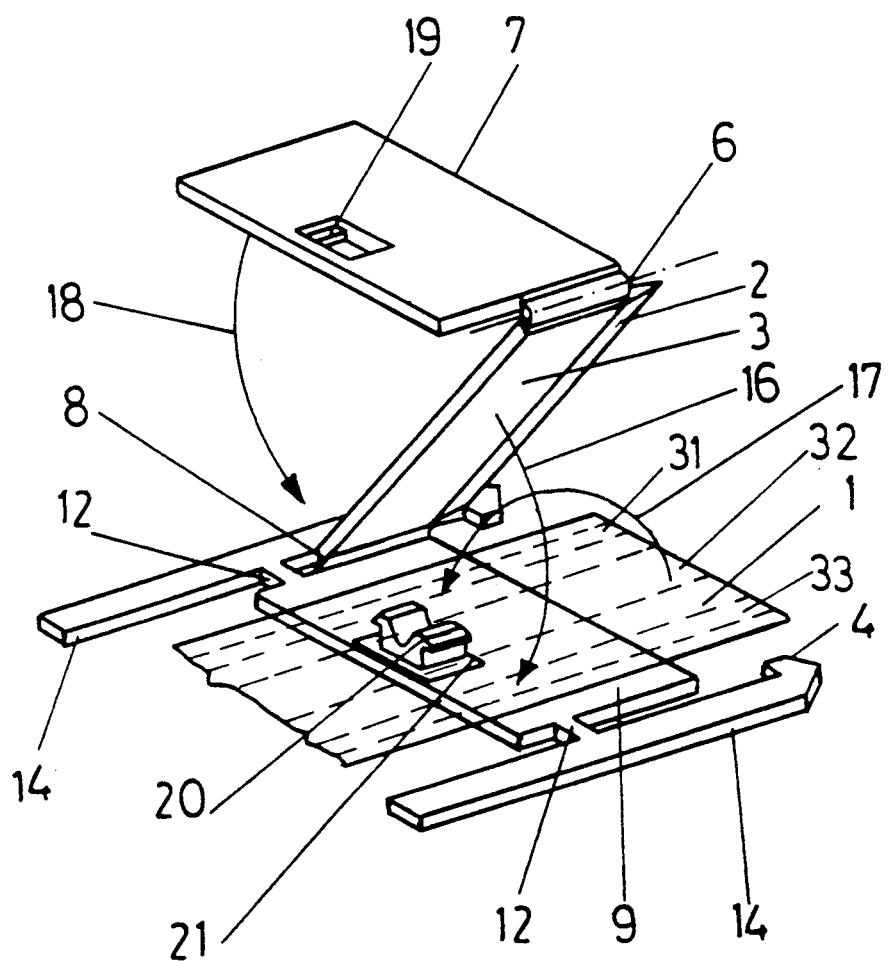
FIG. 3 is a similar view showing a second embodiment of a connection between a tongue and a shaped portion.

The embodiment shown in FIG. 3 differs from that shown in FIGS. 1 and 2 with regard to the manner of the fixing of the tongue 1 and the shaped portion 3. Both the flexible film hinge 6 which connects the shaped portion 3 to the clamping plate 7 and a flexible film hinge 8 for connecting the shaped portion 3 and the cover plate 9 extend parallel to the longitudinal direction of the tongue 1 in this embodiment. The procedure for connecting the tongue 1 to the shaped portion 3 now provides that firstly the shaped portion 3 is pivoted about the film hinge 8 in the direction indicated by the arrow 16. The free end of the tongue 1 is then bent around the edge 2 of the shaped portion 3 in the direction indicated by the arrow 17 and then the clamping plate 7 is pivoted about the film hinge 6 in the direction indicated by the arrow 18 in order to hold the free end of the tongue 1 fast on the shaped portion 3. The resultant pack consisting of the shaped portion 3, the clamping plate 7 and the cover plate 9 is fixed by a retaining connection formed by the press fastener 20 and the retaining opening 19.

In the embodiment shown in FIG. 3 the arms 14 are secured by limbs 12 to the cover plate 9. However, as shown in FIG. 2, arms 14 also could be connected to the shaped portion 3. This would make it possible for the plug connector 23 illustrated in FIGS. 1 and 2 to be employed selectively in conjunction with the stiffened tongue shown in FIG. 1 or FIG. 3.

Figure 4:
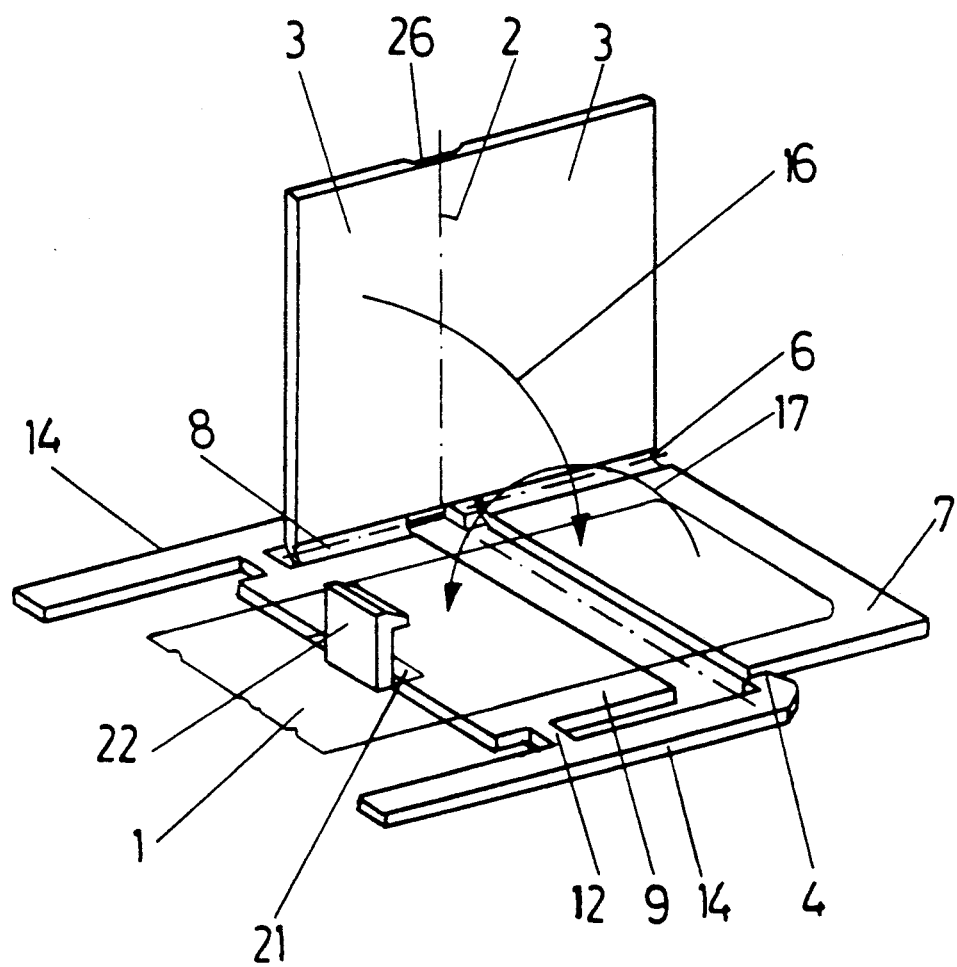
FIGS. 4 and 5 are similar views showing further embodiments thereof.

In the embodiment shown in FIG. 4 the tongue 1 once again is laid with its downwardly facing conductive side on to the clamping plate 7 and the cover plate 9, with a clasp 22 passing through the opening 21 in the tongue 1. Then the shaped portion 3 is pivoted about the film hinges 6 and 8 in the direction indicated by the arrow 16, and positioned over the clamping plate 7 on the one hand and to the cover plate 9 on the other hand. The end edge 2, which is essential to the invention, of the shaped portion 3 is first produced however by folding of the plate 7 and the part of shaped portion 3 positioned thereover in the direction indicated by the arrow 17, that being permitted by a notch 26 in the shaped portion 3. The pack which now consists of four layers is fixed by the clasp 22. With regard to the configuration of the associated plug connector 23, since the projections 4 in this embodiment are displaced downwardly relative to the edge 2 of the shaped portion 3, therefore the openings 13 on the pug connector 23 are also displaced in comparison with the construction shown in FIG. 1.

Figure 5:
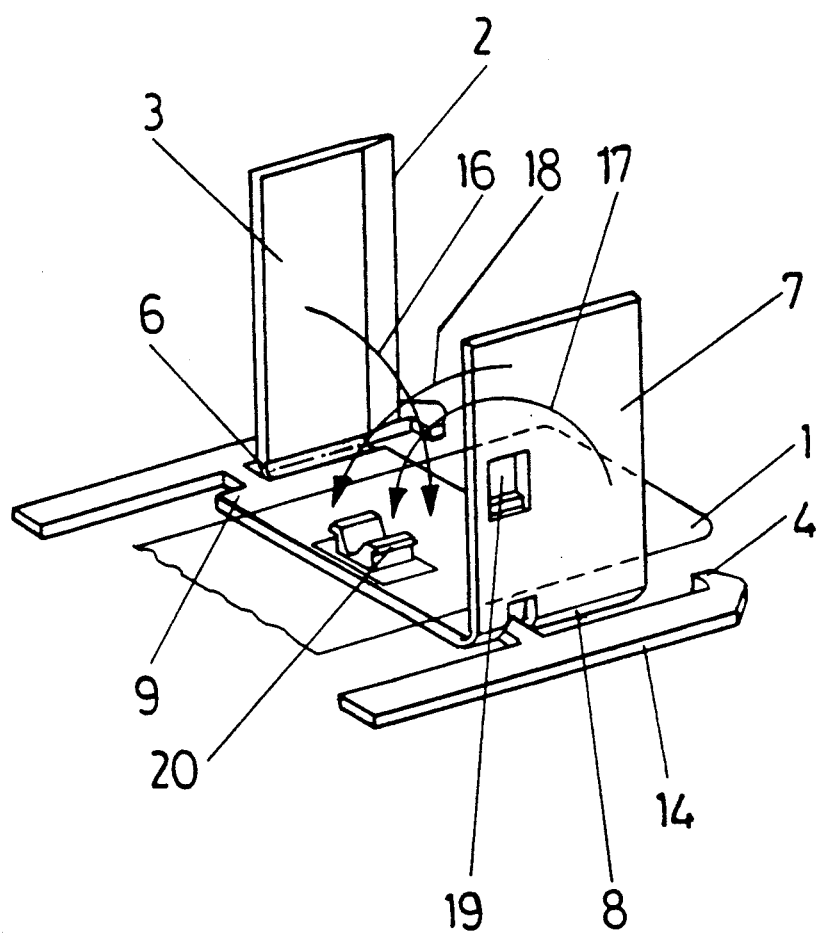

In the embodiment illustrated in FIG. 5 the tongue 1 first is placed on the cover plate 9, just as in the embodiment shown in FIG. 3, and then the shaped portion 3 is pivoted about the film hinge 6 in the direction indicated by the arrow 16. The tongue 1 then is pivoted about the edge 2 of the shaped portion 3 in the direction indicated by the arrow 17. The tongue 1 is fixed in position by the clamping plate 7 being folded down in the direction indicated by the arrow 18 and by anchoring of the press fastener 20 in the retaining opening 19.

All the illustrated embodiments have a number of advantages in common:

By virtue of the fact that the arms 14 bear against the outside of the plug connector, the contact space is closed off outwardly in a practically fluid-tight fashion. Arranging the arms 14 at opposite sides prevents the plug connection from being unintentionally disengaged.

The more contacts that are required, the greater is the advantage afforded by contacting of the tongue at the end edge, in comparison with the state of the art which involves contacts arranged at the sides.

If the connections do not have to be of a guaranteed polarity relationship on the side of the electrode, the connecting socket on the side of the cable may be adapted to be used symmetrically, with the same handling involvement, thereby simplifying use.

I claim:

1. A flexible surface electrode for use in carrying current to and from the skin of a human body, said electrode comprising:

an insulating carrier having opposite sides and including a projecting tongue;

at least one electrically conductive foil on one side of said carrier and extending along said tongue;

a plate-shaped stiffening member having an end edge;

said tongue being bent around said end edge of said stiffening member with said foil facing outwardly and away therefrom;

a clamping plate clamping an end portion of said tongue against said stiffening member with said foil being exposed at said end edge; and a cover plate covering a portion of said tongue extending from said end edge of said stiffening member toward the remainder of said carrier.

2. An electrode as claimed in claim 1, wherein said end edge of said stiffening member is formed by opposite converging surfaces.

3. An electrode as claimed in claim 1, wherein said clamping plate is connected to said stiffening member by a flexible hinge.

4. An electrode as claimed in claim 3, wherein said cover plate is connected to said stiffening member by another flexible hinge.

5. An electrode as claimed in claim 3, wherein said cover plate is connected to said clamping plate by two spaced flexible curved portions extending in a longitudinal direction of said tongue.

6. An electrode as claimed in claim 5, wherein said flexible hinge extends transverse to said direction.

7. An electrode as claimed in claim 6, wherein said end edge of said stiffening member has opposite sides having recesses, and said spaced flexible curved portions fit in respective said recesses.

8. An electrode as claimed in claim 7, wherein said two spaced flexible curved portions are separated by an opening, and said end edge of said stiffening member extends through said opening.

9. An electrode as claimed in claim 1, wherein said stiffening member is connected to said cover plate by a flexible hinge, and said clamping plate is connected to said cover plate by another flexible hinge.

10. An electrode as claimed in claim 9, wherein said flexible hinges are parallel and on opposite side edges of said cover plate.

11. An electrode as claimed in claim 9, wherein said flexible hinges extend parallel to a longitudinal direction of said tongue.

12. An electrode as claimed in claim 1, wherein said stiffening member, said clamping plate and said cover plate are arranged in a stack.

13. An electrode as claimed in claim 12, further comprising means for clamping said stack together.

14. An electrode as claimed in claim 1, further comprising projections connected to one of said stiffening member, said clamping plate or said cover plate for, upon said electrode being plugged into a connector, preventing said electrode from being withdrawn therefrom.

15. An electrode as claimed in claim 14, wherein said projections are provided on respective arms that are connected by respective limbs to respective sides of one of said stiffening member, said clamping plate, or said cover plate.

16. An electrode as claimed in claim 15, wherein said limbs are resilient.

17. An electrode as claimed in claim 15, wherein said arms extend parallel to a longitudinal direction of said tongue.

18. An assembly including said electrode as claimed in claim 1, said electrode including projections or recesses, a plug connector comprising a sleeve having an interior and an open end, at least one spring clip located in said interior for, upon said end edge of said electrode being inserted into said open end, electrically contacting said exposed foil, and said sleeve having at opposite sides thereof recesses or projections for cooperation with respective said projections or recesses of said electrode to maintain said electrode connected to said connector.

19. An assembly as claimed in claim 18, wherein said at least one spring clip has an open mouth facing toward said open end.

* * * * *